(12) United States Patent
Hall

(10) Patent No.: US 9,809,791 B1
(45) Date of Patent: *Nov. 7, 2017

(54) BIOCHEMICAL REACTOR WITH A LOWER DIVIDER SUPPORT STRUCTURE

(71) Applicant: MIH WATER TREATMENT, INC., Danville, CA (US)

(72) Inventor: Peter J. Hall, Danville, CA (US)

(73) Assignee: MIH WATER TREATMENT, INC., Danville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/468,047

(22) Filed: Mar. 23, 2017

Related U.S. Application Data

(63) Continuation of application No. 15/358,050, filed on Nov. 21, 2016.

(51) Int. Cl.
| | |
|---|---|
| *C12M 1/00* | (2006.01) |
| *C12M 1/08* | (2006.01) |
| *C12M 1/40* | (2006.01) |
| *C12M 1/04* | (2006.01) |

(52) U.S. Cl.
CPC ............ *C12M 23/34* (2013.01); *C12M 27/18* (2013.01); *C12M 29/00* (2013.01); *C12M 29/06* (2013.01)

(58) Field of Classification Search
CPC ...... C12M 23/34; C12M 25/20; C12M 27/20; C12M 27/24; C12M 29/04; C12M 21/04; C12M 29/18; Y10S 435/801; Y10S 210/903

See application file for complete search history.

(56) References Cited

U.S. PATENT DOCUMENTS

| | | | |
|---|---|---|---|
| 3,586,294 A | 6/1971 | Strong | |
| 4,350,588 A * | 9/1982 | Tsubota | C02F 3/28 210/197 |

(Continued)

OTHER PUBLICATIONS

Non-Final Office Action issued in corresponding U.S. Appl. No. 15/358,066 dated May 3, 2017.

(Continued)

*Primary Examiner* — Gautam Prakash
(74) *Attorney, Agent, or Firm* — Pillsbury Winthrop Shaw Pittman, LLP

(57) ABSTRACT

This disclosure describes a biochemical reactor with a lower divider support structure. The biochemical reactor may include a tank configured to house immobilized carriers and fluid. The biochemical reactor may include a circulation conduit at least partially disposed within the tank. The circulation conduit may include a circulation outlet opening. The biochemical reactor may include one or more vanes disposed proximate to the circulation outlet opening. The biochemical reactor may include a tank recirculation port disposed proximate to a second end. The biochemical reactor may include a tank inlet configured for feeding fluid into the tank. The biochemical reactor may include a tank outlet configured for drawing fluid from the tank. The tank outlet may be disposed proximate to a first end. The biochemical reactor may include a first divider and a second divider. The second divider may include a support structure including a grating configured to withstand variable loads.

9 Claims, 9 Drawing Sheets

(56) References Cited

U.S. PATENT DOCUMENTS

| | | | | |
|---|---|---|---|---|
| 4,565,552 | A | * | 1/1986 | Cotton ................ C05F 17/0018 |
| | | | | 210/603 |
| 5,447,629 | A | * | 9/1995 | Chaumont et al. ....... C02F 3/10 |
| | | | | 210/150 |
| 5,702,604 | A | * | 12/1997 | Yamasaki et al. ..... B01D 53/18 |
| | | | | 210/151 |
| 5,811,259 | A | | 9/1998 | Hall |
| 5,863,119 | A | | 1/1999 | Yergovich et al. |
| 2001/0027948 | A1 | * | 10/2001 | Tipton et al. ............. C02F 3/10 |
| | | | | 210/629 |
| 2002/0114866 | A1 | | 8/2002 | Kartchner |
| 2002/0185436 | A1 | | 12/2002 | Byers |
| 2004/0050764 | A1 | | 3/2004 | Perriello |
| 2006/0060524 | A1 | | 3/2006 | Chynoweth et al. |
| 2010/0035343 | A1 | | 2/2010 | Cheng |
| 2010/0261226 | A1 | | 10/2010 | Niazi |
| 2011/0091955 | A1 | | 4/2011 | Constantz |
| 2011/0287404 | A1 | | 11/2011 | Niazi |
| 2013/0220829 | A1 | | 8/2013 | Rigby |
| 2014/0238933 | A1 | | 8/2014 | Gencer |

OTHER PUBLICATIONS

Non-Final Office Action issued in corresponding U.S. Appl. No. 15/358,059 dated May 15, 2017.

Non-Final Office Action issued in corresponding U.S. Appl. No. 15/358,054 dated May 16, 2017.

Non-Final Office Action issued in corresponding U.S. Appl. No. 15/358,050 dated May 19, 2017.

Non-Final Office Action issued in corresponding U.S. Appl. No. 15/468,033 dated May 3, 2017.

Non-Final Office Action issued in corresponding U.S. Appl. No. 15/468,038 dated May 15, 2017.

Non-Final Office Action issued in corresponding U.S. Appl. No. 15/468,043 dated May 15, 2017.

Non-Final Office Action issued in corresponding U.S. Appl. No. 15/468,028 dated May 4, 2017.

* cited by examiner

BIOCHEMICAL REACTOR WITH A LOWER DIVIDER SUPPORT STRUCTURE

CROSS-REFERENCE TO RELATED APPLICATIONS

This application is a continuation of U.S. patent application Ser. No. 15/358,050 filed on Nov. 21, 2016 and entitled "BIOCHEMICAL REACTOR WITH A LOWER DIVIDER SUPPORT STRUCTURE," which is incorporated herein by reference in its entirety.

FIELD OF THE DISCLOSURE

This disclosure relates to a biochemical reactor with a lower divider support structure.

BACKGROUND

Biochemical reactors which circulate fluid may be used in a variety of applications. Biochemical reactors may utilize biodegradation performed by microorganisms within the reactor. The biodegradation may be used to produce desired products, to remove specific elements or compounds from ground water and waste water, to perform conversion of ground water and waste water, and/or other utilizations. For example, biochemical reactors may be used for both nitrification (ammonia removal) and denitrification (nitrate removal).

SUMMARY

Biochemical reactors may be configured to accommodate immobilized carriers, porous materials that provide a large surface area upon which live microorganisms are immobilized. Due to the microorganisms' affinity to the carrier material, the microorganisms (e.g., bacteria) may be maintained or confined within the reactor and may be highly concentrated. Biodegradation within a biochemical reactor utilizing immobilized carriers may proceed as raw fluid or influent is fed to the reactor and stirred or agitated such that the liquid comes into contact with the immobilized carriers.

Bioreactors may be capable of performing highly specific reactions by utilizing the biodegradation by the microorganisms. Bioreactor applications may include production of alcohol and antibiotics, removal of trace petroleum hydrocarbons and nitrogen from ground water and waste water, removal of nitrates from ground water, waste water, or salt water, and/or other applications. For example, bioreactors may be utilized in denitrification systems which treat aquatic salt water from commercial aquariums or ground water contaminated with chemical fertilizers.

Current solutions for biological treatment systems may utilize suspended-growth, continuously stirred biochemical tank reactors, or attached growth systems which use solid media to support the bacteria by which biodegradation is achieved. Such biochemical reactor designs may be characterized by activated sludge systems that use large water tanks and problematically yield effluents containing large amounts of sludge, which must be removed by yet another treatment process. Other biological reactors including trickling filters or sand filters, which are smaller and have lower effluent biological solids content, may be plagued with media clogging, poor fluid flow characteristics, and loss of active bacteria.

Efficient utilization of immobilized carriers may be challenging with conventional systems. Immobilized carriers may become very buoyant due to gases which are produced during many biodegradation processes. Due to the high buoyancy of the immobilized carriers, it may be difficult to continuously stir or circulate the immobilized carriers within the raw fluid. Continuously stirring or circulating the immobilized carriers within the raw fluid may ensure efficient biodegradation. For example, immobilized carriers in biochemical reactors used in denitrification systems may generate nitrogen gas during the biodegradation process and may tend to float to the top of the reactor such that they are difficult to stir or circulate within the reactor. Therefore, uniform distribution of the immobilized carriers in bioreactors under high nitrite loading conditions may be difficult.

Conventional bioreactors may include an impeller within the bioreactor to stir and disperse the immobilized carriers within the fluid in the reactor. However, immobilized carriers are particularly fragile, and such impellers impart shear stress on the immobilized carriers to an extent that the immobilized carriers may become damaged. Moreover, during a start-up period of conventional bioreactors, it may be difficult to remove or dislodge immobilized carriers disposed at the bottom of the tank such that the immobilized carriers are circulated throughout the bioreactor tank.

One aspect of the disclosure relates to a biochemical reactor with a lower divider support structure. The biochemical reactor may include a tank configured to house immobilized carriers and fluid. The tank may include a first end and a second end. The immobilized carriers may include porous materials and live microorganisms immobilized on a surface of the porous materials. The immobilized carriers may be configured to remove one or more contaminants from the fluid. The biochemical reactor may include a circulation conduit at least partially disposed within the tank. The circulation conduit may include a circulation inlet opening and a circulation outlet opening. The circulation outlet opening may be disposed proximate to the second end. The biochemical reactor may include one or more vanes disposed proximate to the circulation outlet opening. The one or more vanes may be configured to cause the immobilized carriers and the fluid exiting the circulation outlet opening to enter into a helical pattern as the immobilized carriers and the fluid recirculate through the tank. The biochemical reactor may include a tank recirculation port disposed proximate to the second end. The tank recirculation port may be configured such that fluid is drawn from the tank through the tank recirculation port. The biochemical reactor may include a tank inlet configured for feeding fluid into the tank. The biochemical reactor may include a tank outlet configured for drawing fluid from the tank. The tank outlet may be disposed proximate to the first end. The biochemical reactor may include a first divider having a perforated area. The first divider may include a disk shaped membrane mounted along an axis perpendicular to a central axis of the circulation conduit. The first divider may be disposed between the circulation inlet opening and the tank outlet for separating fluid from the immobilized carriers. The biochemical reactor may include a second divider having a perforated area. The second divider may include a disk shaped membrane mounted along an axis perpendicular to the central axis of the circulation conduit. The second divider may be disposed between the circulation outlet opening and the second end for separating fluid from the immobilized carriers. The first divider perforated area may provide fluid communication between the tank outlet and a tank recirculation area. The tank recirculation area may include one or more regions between the first divider and the second divider. The first divider may be configured such that no immobilized carriers exit the tank via the tank outlet. The second divider perforated area may provide fluid communication between the tank recirculation port and the tank recirculation area. The second divider may be configured such that no immobilized carriers exit the tank via the recirculation port. The second divider may include a support structure configured to withstand variable loads. The support structure may include a grating disposed between the second divider and the second end. The variable loads may include one or more pressures excreted by fluid within the tank and the circulation conduit.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
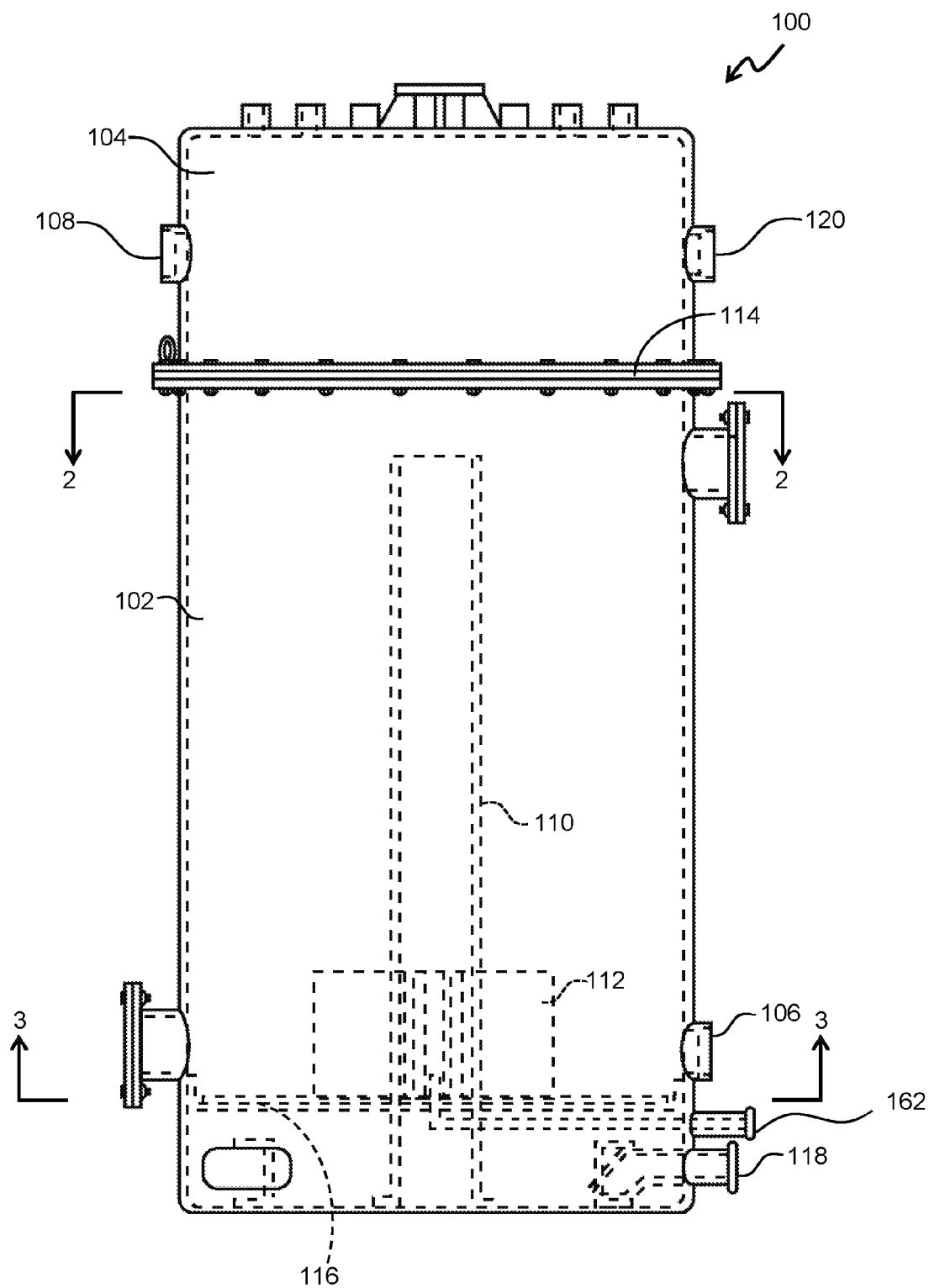
FIG. 1 illustrates a side view of a biochemical reactor, in accordance with one or more implementations.

FIGS. 1-7 illustrate a biochemical reactor 100 which contains immobilized carriers 201 and a fluid such that biodegradation by microorganisms immobilized on the carriers may be utilized. In some implementations, biochemical reactor 100 may include a tank 102, a tank inlet 106, a tank outlet 108, a circulation conduit 110, one or more vanes 112, an unclogging pipe 162, one or more side nozzles 164, a feed conduit 142, a first tank recirculation port 120, a second tank recirculation port 118, a first divider 114, a second divider 116, a grating 166, and/or other components. In some implementations, biochemical reactor 100 may be configured for denitrification, the removal of nitrates from ground water, waste water, salt water, or aquarium water. In some implementations, biochemical reactor 100 may be utilized for nitrification or methane fermentation. In some implementations, biochemical reactor 100 may be utilized for reducing a level of ammonium nitrogen in fluids.

Figure 4:
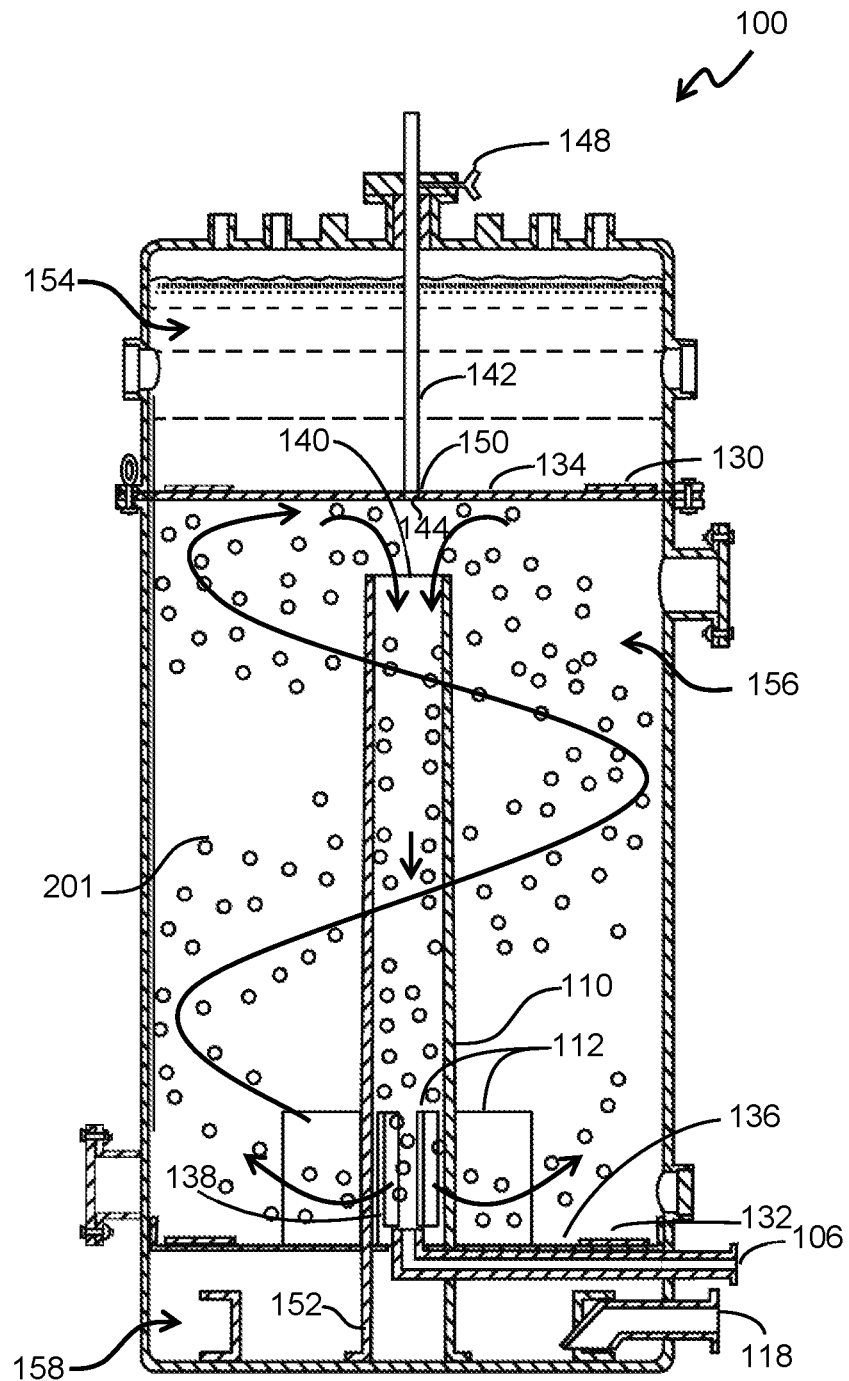
FIG. 4 illustrates a side and sectional operational view of a biochemical reactor, in accordance with one or more implementations.

FIG. 1 illustrates a side view of a biochemical reactor 100, in accordance with one or more implementations. In some implementations, biochemical reactor 100 may include a tank 102. Tank 102 may have a substantially cylindrical shape and/or other shapes. Tank 102 may be configured to hold a fluid such as water and immobilized carriers (e.g., immobilized carriers 201 as illustrated in FIG. 4). Tank 102 may include a tank inlet 106 disposed proximate to a second end (e.g., bottom) of tank 102. Tank 102 may include a tank outlet 108 disposed proximate to a first end (e.g., top) of tank 102. In some implementations, tank inlet 106 and tank outlet 108 may be circular holes or ports disposed within a wall of tank 102. In some implementations, tank inlet 106 and tank outlet 108 may include overflow walls, internal conduits, hoses, and/or other configurations.

In some implementations, influent (e.g., raw, untreated, contaminated, partially treated, and/or other fluids), may enter an interior of tank 102 through tank inlet 106. In some implementations, effluent (e.g., treated fluid) may exit the interior of tank 102 through tank outlet 108.

In some implementations, the size of the tank 102 may be proportional to a desired volumetric flow rate of fluid into inlet 106. For example, if one gallon per minute (gpm) of influent enters tank inlet 106, and it is desired that the influent have at least a 30 minute retention time within the interior of tank 102, tank 102 may have a volumetric capacity of at least 30 gallons, between 40 and 60 gallons, and/or other capacities. In some implementations, tank 102 capacity may be dependent on a capacity of the pumps used with tank 102.

In some implementations, tank 102 may include a cover 104. In some implementations, tank outlet 108 may be disposed in cover 104. In some implementations, tank 102 may be formed from two pieces. In some implementations, tank 102 may be fabricated in one integral piece, from a plurality of pieces, and/or other constructions facilitating tank 102 to hold fluid. In some implementations, cover 104 may attach to a first divider 114 proximate the first end.

In some implementations, first divider 114 may include a top disk 134 which spans the width of tank 102 such that top disk 134 intersects a periphery of tank 102. In some implementations, a second divider 116 may be disposed proximate to the second end. Second divider 116 may span the width of tank 102. In some implementations, second divider 116 may be mounted to an interior surface of tank 102. In some implementations, first divider 114 and second divider 116 may be substantially perpendicular to tank 102 wall. In some implementations, first divider 114 and/or second divider 116 may be disposed at an angle with tank 102 wall. In some implementations, first divider 114 and/or second divider 116 may include a flat surface, an irregular surface, an asymmetrical surface, and/or other surfaces.

Figure 2:
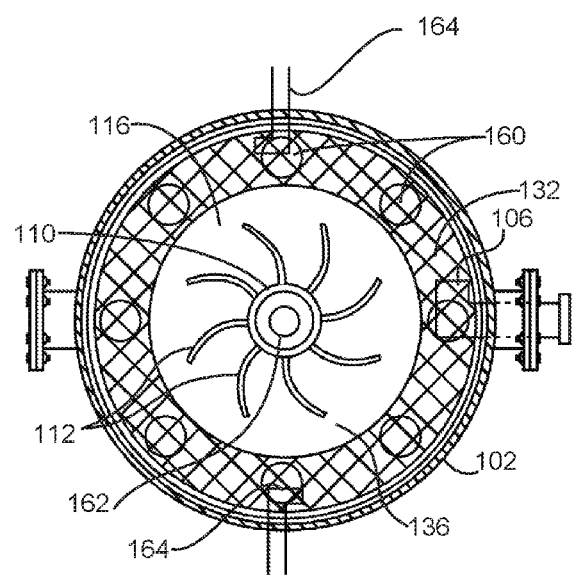
FIG. 2 illustrates a cross-sectional view of the biochemical reactor taken along the line 2-2 of FIG. 1, in accordance with one or more implementations.

By way of a non-limiting example, FIG. 2 illustrates a cross-sectional view of biochemical reactor 100 taken along the line 2-2 of FIG. 1, in accordance with one or more implementations. As shown in FIG. 2, second divider 116, similar to first divider 114, may include a bottom disk 136 and a perforated member 132. Top disk 134 and bottom disk 136 may be circular. In some implementations, Top disk 134 and bottom disk 136 may be constructed from flat sheets of fiber reinforced plastic and/or other materials having a plurality of holes 160 equidistantly or substantially equidistantly spaced near a periphery of top disk 134 and bottom disk 136. For example, the plurality of holes 160 may be disposed radially outwardly from the center of top disk 134 and bottom disk 136.

In some implementations, individual ones of first divider 114 and/or second divider 116 may include perforated members 130 and 132 respectively. In some implementations, perforated members 130 and 132 may include thin and porous screen-like sheets. In some implementations, perforated members 130 and 132 may define a perforated area of first divider 114 and second divider 116 respectively. In some implementations, perforated members 130 and 132 may be annulus shaped, ring shaped, and/or shaped by a region bounded by two concentric circles. In some implementations, perforated members 130 and 132 may be sized to cover all of holes 160 in top disk 134 and bottom disk 136. In some implementations, perforated members 130 and 132 may not cover a center area of top disk 134 and bottom disk 136.

In some implementations, perforated members 130 and 132 may be formed from ⅛ inch thick polyvinylchloride (PVC) having ⅛ inch diameter holes and/or other components. In some implementations, perforated members 130 and 132 may function as a screen, filter, sieve, strainer, net, mesh, sponge, and/or other device by which immobilized carriers 201, individual ones of immobilized carriers 201 having a diameter of approximately ¼ inch, are prevented from passing there through. In some implementations, depending upon a size of immobilized carrier 201, differently sized and configured perforated members 130 and 132 may be utilized. In some implementations, top disk 134 and bottom disk 136 may be formed with a series of holes or perforations such that the perforated areas are part of top disk 134 and bottom disk 136. In some implementations, individual ones of first divider 114 and second divider 116 may be formed from one item having perforations therein. In some implementations, first divider 114 may be formed from multiple items including at least top disk 134, perforated member 130, and/or other items. In some implementations, second divider 116 may be formed from multiple items including at least bottom disk 136, perforated member 132, and/or other items. In some implementations, the perforated area of first divider 114 and second divider 116 may not be disposed proximate to a periphery of first divider 114 and second divider 116. In some implementations, the perforated area of first divider 114 and second divider 116 may not be annularly-shaped.

Returning to FIG. 1, biochemical reactor 100 may include one or more vanes 112 disposed proximate to circulation outlet opening 138 (described below in connection with FIG. 4). One or more vanes 112 may be configured to cause immobilized carriers 201 and the fluid exiting circulation outlet opening 138 to enter into a helical pattern as immobilized carriers 201 and the fluid recirculate through tank 102. In some implementations, one or more vanes 112 may direct immobilized carriers 201 such that immobilized carriers 201 rotate about a longitudinal axis of circulation conduit 110 (described below in connection with FIG. 4) while also circulating through the interior of the circulation conduit 110 and the interior of tank 102. The helical circulation of immobilized carriers 201 may facilitate uniform distribution of immobilized carriers 201 throughout carrier zone 156 (described below in connection with FIG. 4) in biochemical reactor 100.

As shown in FIG. 2, there may be eight (for example) curved vanes 112, with individual vanes immediately adjacent a respective one of the openings forming circulation outlet opening 138. Vanes 112 may be attached to an exterior surface of circulation conduit 110 by fiber reinforced plastic and/or other configurations. In some implementations, vanes 112 may be spaced from circulation opening 138. In some implementations, vanes 112 may be curved to help induce the helical movement of immobilized carriers 201 and fluid about circulation conduit 110. In some implementations, vanes 112 may not extend into perforated member 132 such that immobilized carriers 201 and fluid exiting circulation outlet opening 138 are not forced to immediately "bounce" or reflect off the sides of the interior surface of tank 102. In some implementations, vanes 112 may be interchanged with other apparatus for helically moving immobilized carriers 201 in fluid motion about circulation conduit 110. For example, vanes 112 may be interchanged with at least one helically shaped blade at least partially extending around a periphery of circulation conduit 110. In some implementations, vanes 112 may be interchanged with at least one straight, curved, or angled blade, plate, or fin.

In some implementations, biochemical reactor 100 may include one or more one or more side nozzles 164. The one or more side nozzles 164 may be configured to induce a tangential flow of fluid within tank 102. In some implementations, the one or more side nozzles 164 may be disposed proximate to circulation inlet opening 140 (described below in connection with FIG. 4). In some implementations, the one or more side nozzles 164 may include a portion extending parallel to the interior surface of tank 102 such that a tangential flow of fluid is induced within tank 102.

In some implementations, the one or more side nozzles 164 may comprise at least four side nozzles. In some implementations, the at least four side nozzles 164 may be disposed proximate to first divider 114 and second divider 116. In some implementations, a first nozzle and a second nozzle of the at least four nozzles 164 may be disposed between first divider 114 and second divider 116. In some implementations, the first nozzle and the second nozzle may be located adjacent to first divider 114. In some implementations, a third nozzle and a fourth nozzle of the at least four nozzles 164 may be disposed between first divider 114 and second divider 116. In some implementations, the third nozzle and the fourth nozzle may be located adjacent to second divider 116.

Figure 3:
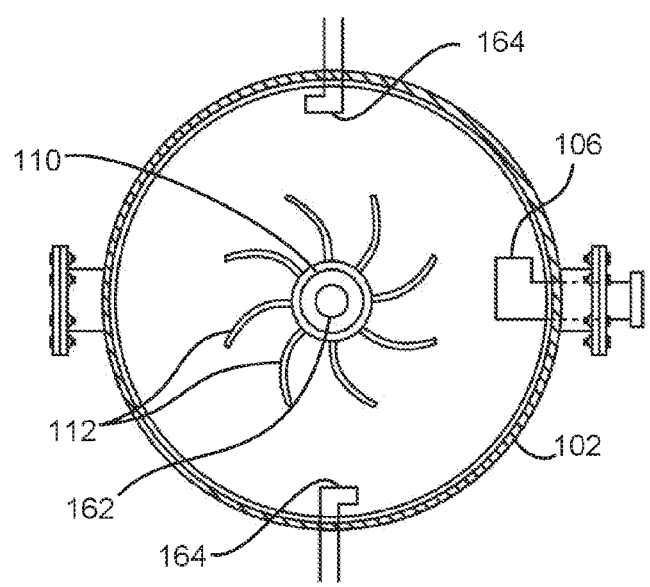
FIG. 3 illustrates a cross-sectional view of the biochemical reactor between lines 2-2 and 3-3 of FIG. 1, in accordance with one or more implementations.

By way of a non-limiting example, FIG. 3 illustrates a cross-sectional view of biochemical reactor 100 between lines 2-2 and 3-3 of FIG. 1, in accordance with one or more implementations. As illustrated in FIG. 3, individual ones of the first nozzle, the second nozzle, the third nozzle, and the fourth nozzle may comprise a first portion. In some implementations, the first portion may extend perpendicular to the interior surface of tank 102. In some implementations, individual ones of the first nozzle, the second nozzle, the third nozzle, and the fourth nozzle may comprise a second portion. In some implementations, the second portion may extend parallel to the interior surface of tank 102. As shown in FIG. 3, the first nozzle may be disposed opposite the second nozzle and the third nozzle may be disposed opposite the fourth nozzle. In some implementations, the first nozzle and the second nozzle may overlap the third nozzle and the fourth nozzle respectively.

In some implementations, the first nozzle, the second nozzle, the third nozzle, and the fourth nozzle may be constructed from stainless steel and/or other materials. In some implementations, individual ones of the first nozzle, the second nozzle, the third nozzle, and the fourth nozzle may comprise a pipe having a diameter of 2 inches and/or other dimensions.

In some implementations, responsive to a high nitrate load, immobilized carriers 201 may become buoyant and accumulate below first divider 114. The first nozzle and the second nozzle may facilitate recirculation of accumulated immobilized carriers 201 by inducing a tangential flow. In some implementations, the first nozzle and the second nozzle may facilitate a separate flow of water below first divider 114 to agitate accumulated immobilized carriers 201 and release entranced nitrogen gas. In some implementations, immobilized carriers may be resting above second divider 116 during treatment of fluids that do not produce nitrogen gas (e.g., perchlorate). In some implementations, the third nozzle and the fourth nozzle may facilitate agitation of immobilized carriers resting above second divider 116.

Returning to FIG. 1, biochemical reactor 100 may include a tank inlet 106. In some implementations, tank inlet 106 may be disposed between first divider 114 and second divider 116. In some implementations, tank inlet 106 may be disposed proximate to second divider 116 such that a time of the fluid being treated by immobilized carriers 201 is maximized. In some implementations, tank inlet 106 may be disposed above second divider 116 such that influent entering biochemical reactor 100 does not damage second divider 116 responsive to a lack of circulation during operation of biochemical reactor 100. For example, second divider 116 may be damaged responsive to circulation flow being stopped during full flow operation if inlet flow is below second divider 116. In some implementations, tank inlet 106 may be disposed such that backflow of water from biochemical reactor 100 and loss of immobilized carriers 201 from biochemical reactor 100 is prevented. In some implementations, tank inlet 106 may be disposed such that a helical fluid flow is induced in tank 102. For example, as shown in FIG. 3, tank inlet 106 may include a portion extending parallel to the interior surface of tank.

In some implementations, tank inlet 106 may be constructed from stainless steel and/or other materials. In some implementations, a diameter of tank inlet 106 may be 4 inches and/or other dimensions. In some implementations, responsive to a differential pressure, strain, and/or curvature of second divider 116 exceeding a predetermined threshold, a fluid flow to tank inlet 106 may be suspended.

In some implementations, biochemical reactor 100 may include one or more pressure sensors configured to convey information related to a differential pressure between first divider 114 and second divider 116. In some implementations, responsive to the differential pressure exceeding the predetermined threshold, the fluid flow to tank inlet 106 may be suspended.

In some implementations, biochemical reactor 100 may include a strain gauge configured to convey information related to a strain on second divider 116. In some implementations, responsive to the strain exceeding the predetermined threshold, the fluid flow to tank inlet 106 may be suspended.

In some implementations, biochemical reactor 100 may include one or more optical sensors configured to convey information related to a curvature of second divider 116. In some implementations, responsive to the curvature exceeding the predetermined threshold, the fluid flow to tank inlet 106 may be suspended.

In some implementations, biochemical reactor 100 may include a tank outlet 108. In some implementations, tank outlet 108 may be disposed proximate the first end. In some implementations, tank outlet 108 may be disposed above first divider 114. In some implementations, first divider 114 may prevent the passage of immobilized carriers 201 to tank outlet 108. In some implementations, first divider 114 may facilitate the fluid being treated to pass through the perforated area such that effluent may be drawn from tank outlet 108.

In some implementations, first divider 114 and second divider 116 may define a first carrier-free zone 154 above first divider 114, a second carrier-free zone 158 below second divider 116, and a carrier zone 156 in the area located between first divider 114 and second divider 116. In some implementations, carrier zone 156 may include an area in which fluid is being treated by immobilized carriers 201. By way of a non-limiting example, FIG. 4 illustrates a side and sectional operational view of biochemical reactor 100, in accordance with one or more implementations. As shown in FIG. 4, carrier zone 156 includes an area within biochemical reactor 100 where immobilized carriers 201 are uniformly or substantially uniformly circulated such that biodegradation by immobilized carriers 201 is utilized.

In some implementations, biochemical reactor 100 may include a circulation conduit 110 at least partially disposed within tank 102. In some implementations, circulation conduit 110 may be disposed within carrier zone 156. In some implementations, circulation conduit 110 may extend outside carrier zone 156, outside tank 102, and/or other configurations. In some implementations, circulation conduit 110 may include a cylindrical and tubular member having an upper end and a lower portion disposed opposite from the upper end. In some implementations, circulation conduit 110 may include a circulation inlet opening 140 and a circulation outlet opening 138. In some implementations, circulation inlet opening 140 may be circular and may be disposed at the upper end of circulation conduit 110. In some implementations, circulation outlet opening 138 may be disposed opposite from circulation inlet opening 140. In some implementations, circulation outlet opening 138 may be disposed at the lower portion of circulation conduit 110. In some implementations, circulation conduit 110 may be positioned along a longitudinal axis of tank 102, along a central axis of tank 102, and/or other positions. In some implementations, circulation conduit 110 is free from any restrictions or tapers which may initiate clogging or packing of immobilized carriers 201 within circulation conduit 110.

In some implementations, a diameter of circulation conduit 110 may be ⅓ to ⅕ of a diameter of tank 102. In some implementations, the diameter of circulation conduit 110 may be ⅕ to ¹⁄₁₀ of the diameter of tank 102. In some implementations, the diameter of circulation conduit 110 may be dependent on a desired capacity of bioreactor 100. For example, the diameter for tank 102 may be approximately 49 inches and the diameter of circulation conduit 110 may be 8 inches. In some implementations, circulation conduit 110 may include an oval tube, a tube with changing diameters, a square tube, and/or other tubes. In some implementations, circulation conduit 110 may be constructed from fiber reinforced plastic and/or other materials.

In some implementations, circulation conduit 110 may include a length at least greater than half the distance between first divider 114 and second divider 116. In some implementations, the length of circulation conduit 110 may be dependent on dimensions of other parts of biochemical reactor 100.

In some implementations, circulation inlet opening 140 may permit fluid and immobilized carriers 201 to enter into circulation conduit 110. In some implementations, circulation outlet opening 138 may permit immobilized carriers 201 and fluid to exit circulation conduit 110. In some implementations, an area of circulation inlet opening 140 and circulation outlet opening 138 may be selected to facilitate immobilized carrier 201 to pass there through.

As shown in FIG. 4, circulation outlet opening 138 may be located in an exterior surface of the circulation conduit 110. In some implementations, a bottom end of circulation conduit 110 may be closed off. In some implementations, the bottom end of circulation conduit 110 may be adjacent to bottom disk 136. In some implementations, fluid traversing through circulation conduit 110 may not be permitted to immediately enter second carrier-free zone 158. In some implementations, bottom disk 136 may block the passage of the fluid in the area immediately surrounding the periphery of circulation conduit 110 near the second end of tank 102. In some implementations, holes 160 formed in bottom disk 136 and covered by the perforated member 132 may permit passage of the fluid to second carrier-free zone 158.

In some implementations, circulation outlet opening 138 may include a series of tubes or pipes extending from circulation conduit 110 at an angle to induce helical motion to immobilized carriers 201 and fluid. In some implementations, circulation outlet opening 138 may include a plurality of slit-shaped openings or slots that extend through the wall of circulation conduit 110. In some implementations, the plurality of slit-shaped openings may be formed in the lower portion of circulation conduit 110. In some implementations, circulation outlet opening 138 may include oval-shaped openings, circular openings, square-shaped openings, curved slits, perforated patterns, and/or other openings facilitating passage of immobilized carriers 201 there through. In some implementations, circulation outlet opening 138 may include eight slit-shaped openings. In some implementations, the eight slit-shaped openings may be equidistantly spaced about the periphery of circulation conduit 110.

In some implementations, a total rectangular net cross-sectional area of the eight slit-shaped openings may be at least equal to the circular cross-sectional area of circulation conduit 110. In some implementations, circulation outlet opening 138 may include an area such that immobilized carriers 201 traversing through circulation conduit 110 do not pack, choke, or clog near the bottom of circulation conduit 110. In some implementations, the net cross-sectional area of circulation outlet opening 138 may be at least 50% greater than the cross-sectional area of circulation conduit 110 to prevent choking of immobilized carriers 201 within circulation conduit 110 at maximum loading conditions. For example, the net cross-sectional area of circulation outlet opening 138 may be approximately 75 square inches, and the cross-sectional area of circulation conduit 110 may be approximately 50 square inches.

Returning to FIG. 1, biochemical reactor 100 may include an unclogging pipe 162. Unclogging pipe 162 may be configured to clear clogging of circulation conduit 110. In some implementations, unclogging pipe 162 may include an unclogging inlet opening and an unclogging outlet opening. In some implementations, second divider 116 may include an aperture. In some implementations, the unclogging outlet opening may be coupled to the second divider 116 aperture. In some implementations, unclogging pipe 162 may extend beyond a surface of second divider 116 into circulation conduit 110. In some implementations, Unclogging pipe 162 may extend along a central axis of circulation conduit 110. In some implementations, unclogging pipe 162 may be constructed from stainless steel and/or other materials. In some implementations, unclogging pipe 162 may have a diameter of ⅜ inch. In some implementations, unclogging pipe 162 may include a flex line configured to prevent unclogging pipe 162 from breaking responsive to a movement of biochemical reactor 100, a movement of unclogging pipe 162, and/or other movements.

In some implementations, the unclogging inlet opening may be coupled to a pressure generating device. In some implementations, responsive to a detection of clogging in circulation conduit 110, pressurized air generated by the pressure generator may be delivered to circulation conduit 110 via the unclogging outlet opening. In some implementations, the pressure generator may be configured to deliver pressurized air during a non-operation period of biochemical reactor 100 to prevent a disruption of biochemical reactor 100 normal operations.

In some implementations, biochemical reactor 100 may include a feed conduit 142. In some implementations, feed conduit 142 may include a feed outlet 144. In some implementations, fluid flow may be directed out of feed outlet 144 into circulation conduit 110. In some implementations, the fluid flow emanating from feed outlet 144 may be obtained by pumping fluid from a first recirculation port 120, a second recirculation port 118, and/or other ports. In some implementations, first recirculation port 120 may be disposed above first perforated member 130 in first carrier-free zone 154. In some implementations, first recirculation port 120 may be configured such that no immobilized carriers 201 exit tank 102 when fluid is drawn from tank 102 by first recirculation port 120. In some implementations, second recirculation port 118 may be disposed below second perforated member 132 in second carrier-free zone 158. Second recirculation port 118 may be configured such that no immobilized carriers 201 exit tank 102 via second recirculation port 118.

As illustrated in FIG. 4, second recirculation port 118 may be formed by a tube having an inlet disposed within second carrier-free zone 158. In some implementations, an end portion of second recirculation port 118 may include a bend such that the inlet opening to second recirculation port 118 is angled downwardly and disposed proximate to the second end of tank 102 to prevent the drawing of immobilized carrier 201 towards perforated member 132.

In FIG. 4, feed conduit 142 may be configured to induce a circulation motion of immobilized carriers 201 and fluid into circulation inlet opening 140. In some implementations, feed conduit 142 may be disposed directly above a center of circulation conduit 110. In some implementations, first divider 114 may include an aperture 150. In some implementations, feed conduit 142 outlet may be coupled to aperture 150. In some implementations, aperture 150 may include a seal (not shown) which prevents immobilized carriers 201 from passing through any space between first divider 114 and an exterior surface of feed conduit 142. In some implementations, feed conduit 142 may not extend beyond a surface of first divider 114 toward second divider 116. In some implementations, feed conduit 142 may be disposed along the central axis of circulation conduit 110. In some implementations, feed conduit 142 outlet may be immovable with respect to circulation inlet opening 140. In some implementations, a threaded clasp-type member 148 may apply a force against the exterior surface of feed conduit 142 to hold feed conduit 142 in place such that feed conduit 142 is immovable with respect to circulation inlet opening 140.

In some implementations, a distance between first divider 114 and circulation inlet opening 140 may be equivalent to a diameter of circulation inlet opening 140. As such, a distance between feed outlet 144 and circulation inlet opening 140 may be equivalent to the diameter of circulation inlet opening 140. For example, the diameter of circulation inlet opening may be 18 inches and the distance between feed outlet 144 and circulation inlet opening 140 may be 18 inches. In some implementations, feed conduit 142 may be rod-shaped. In some implementations, feed conduit 142 may include a cylindrical and hollow tube. In some implementations, feed conduit 142 may be constructed from stainless steel and/or other materials.

In some implementations, the fluid may include one or more contaminants. In some implementations, a flow rate of fluid in feed conduit 142 may be adjusted based on the one or more contaminants and a concentration of the one or more contaminants. In some implementations, responsive to immobilized carriers 201 accumulating proximate first divider 114, the fluid flow rate may be increased. In some implementations, fluid flow out of feed outlet 144 into circulation conduit 110 may induce a circulation motion of immobilized carrier 201 and fluid into circulation inlet opening 140, out of circulation outlet opening 138, through the interior of tank 102, and again into circulation inlet opening 140. In some implementations, the induced flow effect may draw immobilized carriers 201 into circulation conduit 110 at a greater flow rate than the flow rate exiting feed outlet 144. For example, the inlet influent volumetric flow rate into biochemical reactor 100 may be one gpm, the recirculation volumetric flow rate exiting feed outlet 144 may be 10 gpm, and the induced volumetric flow rate of immobilized carriers 201 and fluid through circulation conduit 110 may be approximately 40 to 50 gpm. In some implementations, the velocity of fluid flowing through circulation conduit 110 may be at least 13 ft/s when treating nitrates (a gas producing contaminant). In some implementations, the flow rate may be minimized to prevent unnecessary contact and wear of immobilized carriers 201 when treating non-gas producing contaminants.

In some implementations, circulation inlet opening 140 may include a circulation inlet cross-sectional area of a predetermined relationship to the feed outlet 144 cross-sectional area such that when fluid flow is directed out of feed outlet 144 toward circulation conduit 110, the volumetric circulation flow rate of immobilized carriers 201 and fluid through circulation conduit 110 is at least three times greater than a volumetric flow rate of fluid flow through feed outlet 144. In some implementations, the volumetric circulation flow rate of immobilized carriers 201 and fluid through circulation conduit 110 may be four to ten times greater than the volumetric flow rate of fluid flow through feed outlet 144. For example, circulation inlet cross-sectional area may be at least four times, ten times, and/or other amounts greater than the feed outlet cross-sectional area.

Figure 5:
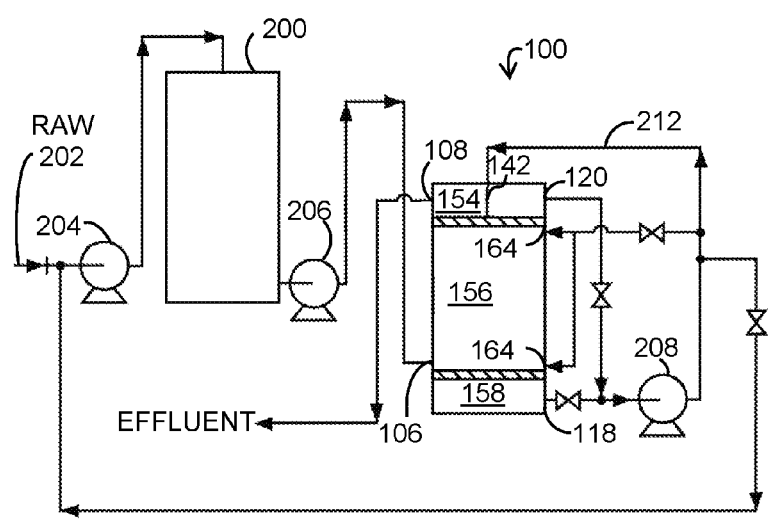
FIG. 5 illustrates a systematic view of a biochemical reactor, in accordance with one or more implementations.

FIG. 5 illustrates a systematic view of a biochemical reactor, in accordance with one or more implementations. In FIG. 5, biochemical reactor 100 may be incorporated in a partial assembly of a denitrification system. The denitrification system may include a deaeration reactor 200 along with biochemical reactor 100. Deaeration reactor 200 may be an implementation of biochemical reactor 100, a series of biochemical reactors 100, and/or other devices for removing oxygen from raw influent. As shown in FIG. 5, the raw influent may be fed to the system at a system inlet 202 where it is pumped into deaeration reactor 200 by a pump 204 to remove oxygen from the influent prior to treatment by bioreactor 100. In some implementations, raw influent may be retained within deaeration reactor 200 for approximately 20-45 minutes and/or other durations. In some implementations, the duration of raw influent retention within deaeration reactor 200 may be dependent on an oxygen content of the raw influent. In some implementations, after sufficient oxygen has been removed from the raw influent, a pump 206 may pump the effluent from deaeration reactor 200 into inlet 106 of biochemical reactor 100.

In some implementations, once fluid is drawn from tank 102 by either first recirculation port 120 and/or second recirculation port 118, a pump 208 may pump the fluid along a recirculation line 212 into feed conduit 142.

In some implementations, an extent to which fluid is drawn from first recirculation port 120 or second recirculation port 118 may depend on a point in time when the denitrification system is operated. Immobilized carriers 201 may not be buoyant at start-up of biochemical reactor 100. In some implementations, immobilized carriers 201 may be disposed proximate to the second end of tank 102, directly above second divider 116. In some implementations, approximately 80% of the recirculation flow may be drawn from first recirculation port 120 and 20% from the second recirculation port 118 at start-up such that immobilized carriers 201 are drawn toward perforated member 130 and circulated in carrier zone 156. In some implementations, after immobilized carriers 201 have begun to circulate, generate gas, and become more buoyant, the operation of biochemical reactor 100 may reach a steady state. In some implementations, approximately 40% of the recirculation flow may be drawn from first recirculation port 120 and 60% from the second recirculation port 118 at steady state.

Figure 6:
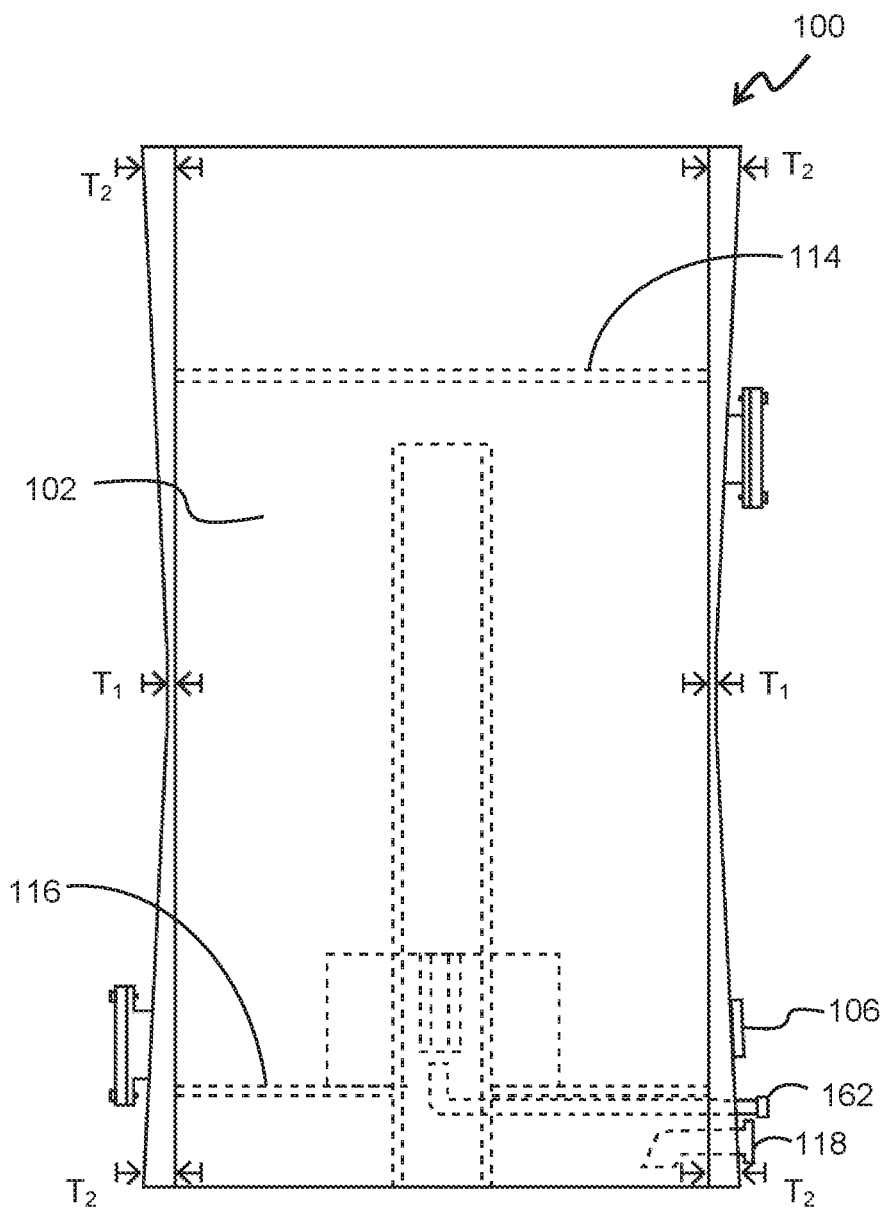
FIG. 6 illustrates a side view of a biochemical reactor with a variable tank thickness, in accordance with one or more implementations.

In some implementations, tank 102 wall may be reinforced to prevent damages from warping. In some implementations, warping of tank 102 sidewalls may be caused by an increased load resistance of second divider (described below in connection with FIG. 7). In some implementations, tank 102 may include a first thickness. In some implementations, at least a portion of tank 102 may include a reinforced structure. In some implementations, the reinforced structure may include a second thickness greater than the first thickness. By way of a non-limiting example, FIG. 6 illustrates a side view of a biochemical reactor with a variable tank thickness, in accordance with one or more implementations. As shown in FIG. 6, a mid-section of tank 102 may include the first thickness $T_1$. In some implementations, first thickness $T_1$ may increase toward the first end and the second end. The first end and the second end may include the second thickness $T_2$. For example, first thickness $T_1$ may be ¼ inch and second thickness $T_2$ may be ⅜ inch. In some implementations, an entirety of tank 102 wall may be thickened.

Figure 7:
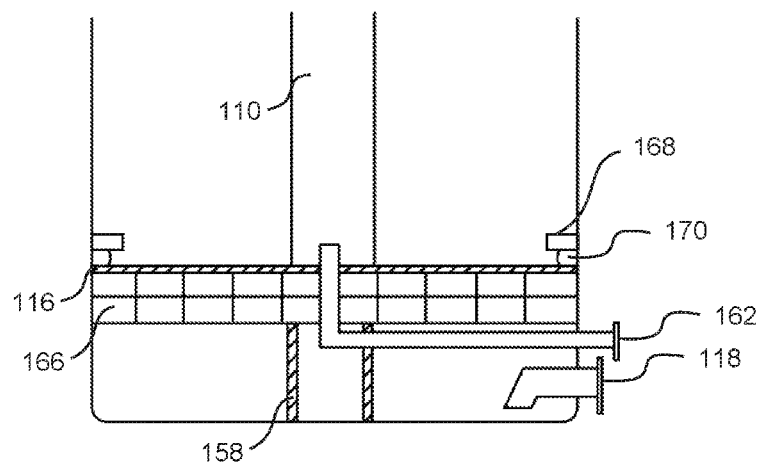
FIG. 7 illustrates a sectional view of a biochemical reactor with a lower divider support structure, in accordance with one or more implementations.

FIG. 7 illustrates a sectional view of a biochemical reactor with a lower divider support structure, in accordance with one or more implementations. As shown in FIG. 7, at least second divider 116 includes a support structure configured to withstand variable loads. In some implementations, the support structure may include a grating 166 disposed between second divider 116 and the second end. In some implementations, the variable loads may include one or more pressures excreted by fluid within tank 102 and circulation conduit 110. In some implementations, the support structure may include a ring 168 disposed above a periphery of second divider 116. In some implementations, a sealant 170 may be disposed between ring 168 and second divider 116 such that, responsive to a deformation of second divider 116, immobilized carriers 201 are entrapped between first divider 114 and second divider 116. In some implementations, sealant 170 may include silicone and/or other materials.

In some implementations, grating 166 may include fiberglass grating. In some implementations, fiber glass grating 166 may include a resin coating. In some implementations, the resin coating may be configured to comply with NSF 60 and NSF 61 requirements. In some implementations, fiberglass grating 166 may have a thickness of four inches and/or other thicknesses. In some implementations, grating 166 may be constructed using stainless steel and/or other materials. In some implementations, stainless steel grating 166 may have a thickness of two inches and/or other thicknesses.

In some implementations, the support structure may include a hollow tube 158 disposed between grating 166 and the second end. In some implementations, hollow tube 158 may be coupled to grating 166 and the second end along the central axis of circulation conduit 110. In some implementations, hollow tube 158 may be configured to provide support for grating 166. For example, hollow tube 158 may prevent a deformation of grating 166. In some implementations, a center of grating 166 may curve, bend, and/or deform due to pressures exerted by fluid within tank 102 and circulation conduit 110. In some implementations, hollow tube 158 may provide support for at least a center of grating 166.

Figure 8:
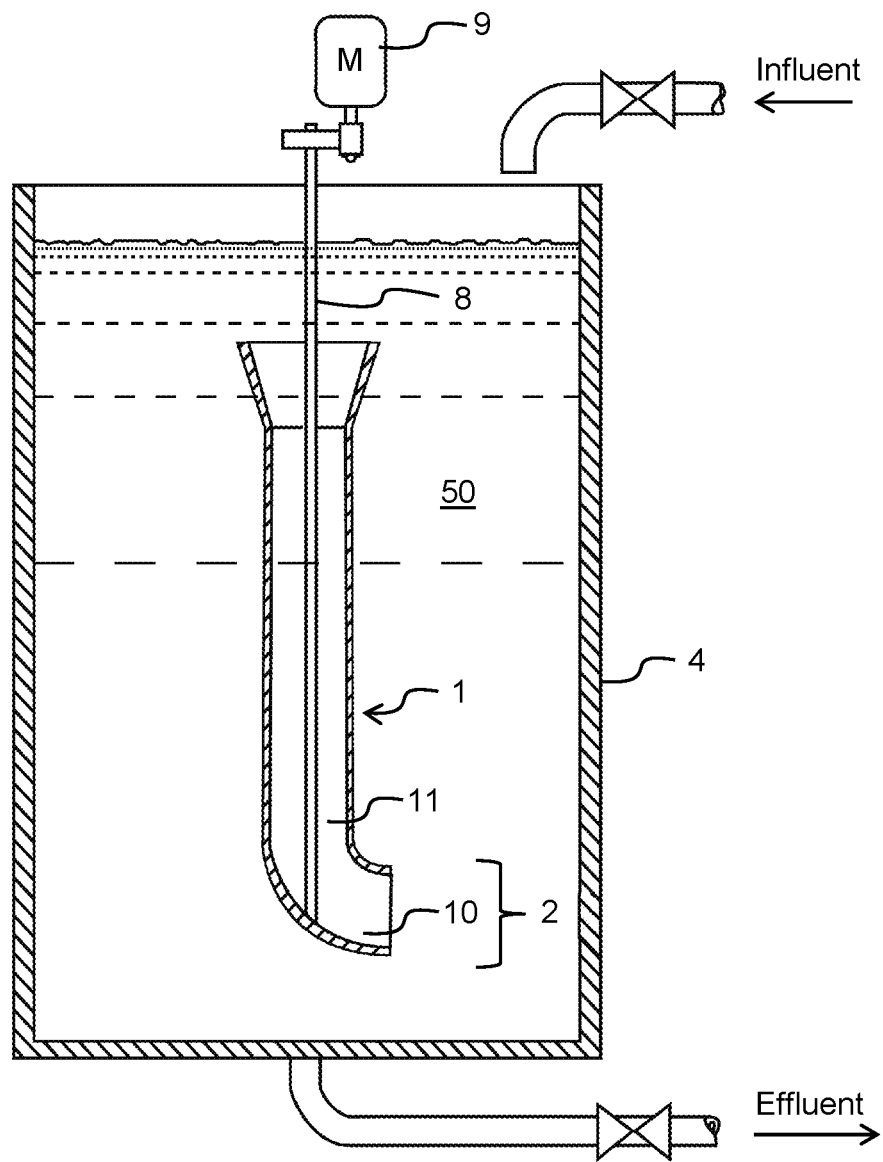
FIG. 8 illustrates a conventional bioreactor with a centrifugal tube, in accordance with one or more implementations.

By way of a non-limiting contrasting example, FIG. 8 illustrates a conventional bioreactor with a centrifugal tube. In FIG. 8, bioreactor 50 may include a centrifugal tube 1. Centrifugal tube 1 may have a curved end 2. Curved end 2 may be disposed proximate to outlet 10. Centrifugal tube 1 may be mounted on a rotary shaft 8 within the interior of the bioreactor tank 4. Centrifugal tube 1 may be rotated such that a centrifugal force is generated. The centrifugal force may draw the immobilized carriers into the top inlet of the centrifugal tube 1, through the interior length 11 of the tube and out of the outlet 10 disposed near the bottom of the reactor. Shaft 8 and centrifugal tube 1 may need to be continuously rotated by a motor 9 to create the centrifugal action.

Bioreactor 50 may include insufficient capabilities when adapted for use in large denitrification systems. For example, due to the presence of many rotating parts within the interior of bioreactor 50, it may be challenging to construct. Additionally, centrifugal tube 1 may need to be extremely large to accommodate flow rates and denitrification requirements with large denitrification systems (e.g., bioreactors used with commercial aquariums). Due to the required size of centrifugal tube 1 for large denitrification systems, centrifugal tube 1 may be difficult to rotate and balance. Therefore, moving parts of the bioreactor 50 may be made from materials accommodating large forces generated when rotating a large centrifugal tube 1. Such materials may be expensive, particularly when the materials need to be corrosion resistant in salt water. Removing high amounts of nitrates may require centrifugal tube 1 to be rotated faster. Faster rotation may create a vortex within the bioreactor, drawing oxygen into the fluid within the reactor. Presence of oxygen within the water may undermine the capabilities of the immobilized carriers to remove nitrates from the water.

Figure 9:
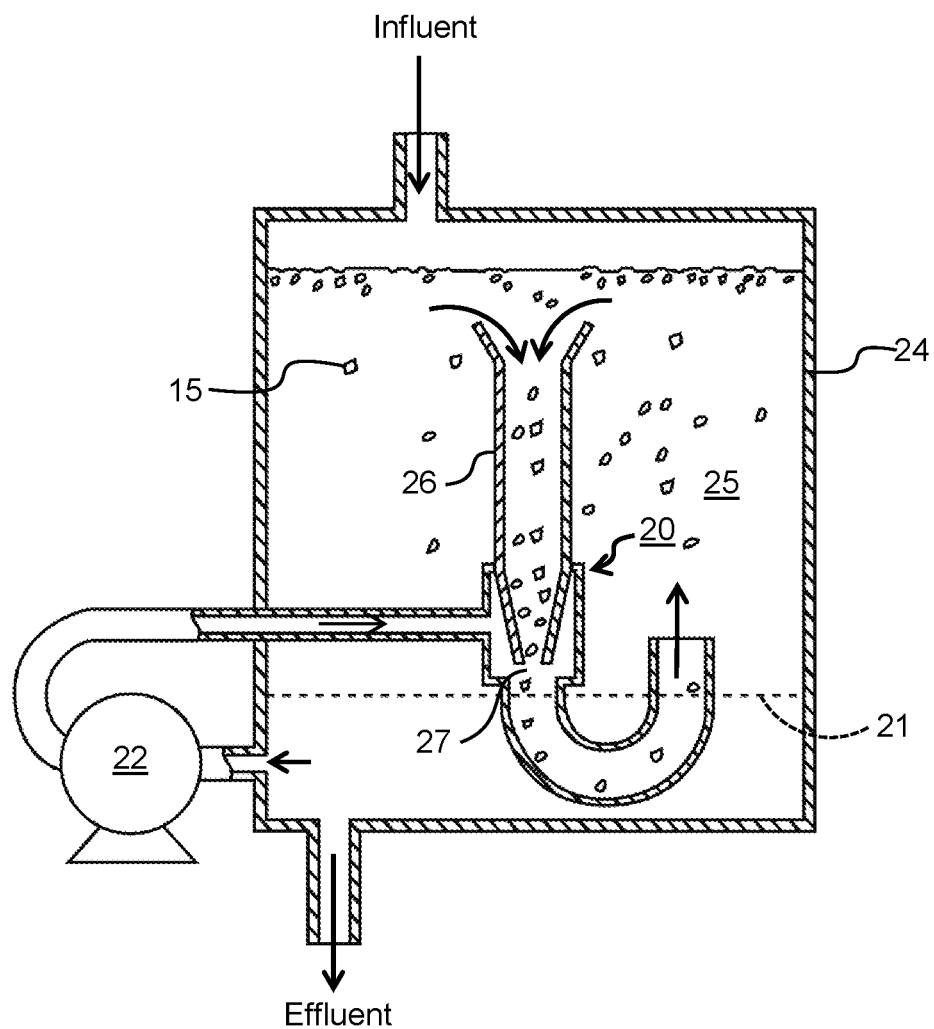
FIG. 9 illustrates a conventional bioreactor with a liquid current jet mechanism powered by an external pump, in accordance with one or more implementations.

By way of a non-limiting contrasting example, FIG. 9 illustrates a conventional bioreactor 25 with a liquid current jet mechanism 20 powered by an external pump 22. Bioreactor 25 may include a filter 21. Filter 21 may separate immobilized carriers 15 from the fluid such that the fluid may be drawn from the bioreactor and delivered to pump 22. Pump 22 may be disposed external of bioreactor vessel 24. Pump 22 may pump the fluid at a high velocity around a bottom opening 27 of a tube 26 such that immobilized carriers and fluid within tube 26 are drawn through bottom opening 27 by the high velocity fluid.

Liquid current jet mechanism 20 may create flow within tube 26 and within the interior of bioreactor vessel 24. Bottom opening 27 may be tapered inward to enhance the suction of immobilized carriers 15 and fluid through tube 26. The tapered design may cause immobilized carriers 15 to pack-up and choke bottom opening 27. Responsive to jet mechanism 20 being clogged or packed, the bioreactor may need to be shut down, drained, and disassembled to unpack immobilized carriers 15 from bottom opening 27.

External pump 22 may generate high flows rates for jet mechanism 20 to provide the amount of suction necessary to properly and uniformly distribute immobilized carriers 15 within bioreactor vessel 24. As such, a large pump may be required for high load. Use of a large pump may decrease the efficiency of bioreactor 25.

Due to jet mechanism 20 being disposed proximate to bottom opening 27, drawing buoyant immobilized carriers 15 into tube 26 inlet may be challenging. Immobilized carriers 15 may float and accumulate on the surface of the fluid within bioreactor vessel 24 before immobilized carriers 15 are drawn into tube 26 inlet. As such, a non-uniform dispersion of immobilized carriers 15 within bioreactor 25 may be caused and the efficiency of, for example, denitrification within bioreactor 25 may be reduced Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A biochemical reactor with a lower divider support structure, the biochemical reactor comprising:

a tank configured to house immobilized carriers and fluid, the tank having a first end and a second end opposite the first end, the immobilized carriers including porous materials and live microorganisms immobilized on a surface of the porous materials, wherein the immobilized carriers are configured to remove one or more contaminants from the fluid;

a circulation conduit at least partially disposed within the tank, the circulation conduit having a circulation inlet opening and a circulation outlet opening;

one or more vanes disposed proximate to the circulation outlet opening, the one or more vanes configured to cause the immobilized carriers and the fluid exiting the circulation outlet opening to enter into a helical pattern as the immobilized carriers and the fluid recirculate through the tank;

a tank recirculation port disposed proximate to the second end, the tank recirculation port configured such that fluid is drawn from the tank through the tank recirculation port;

a tank inlet configured for feeding fluid into the tank;

a tank outlet configured for drawing fluid from the tank, the tank outlet disposed proximate to the first end; and a first divider having a perforated area, the first divider including a disk shaped membrane mounted along an axis perpendicular to a central axis of the circulation conduit, the first divider being disposed between the circulation inlet opening and the tank outlet for separating fluid from the immobilized carriers, and a second divider having a perforated area, the second divider including a disk shaped membrane mounted along an axis perpendicular to the central axis of the circulation conduit, the second divider being disposed between the circulation outlet opening and the second end for separating fluid from the immobilized carriers, wherein the first divider perforated area provides fluid communication between the tank outlet and a tank recirculation area, the tank recirculation area including tank one or more regions between the first divider and the second divider, wherein the first divider is configured such that no immobilized carriers exit the tank via the tank outlet, wherein the second divider perforated area provides fluid communication between the tank recirculation port and the tank recirculation area, and wherein the second divider is configured such that no immobilized carriers exit the tank via the recirculation port;

wherein at least the second divider comprises a support structure configured to withstand variable loads, the support structure including a grating disposed between the second divider and the second end, wherein the variable loads include one or more pressures excreted by fluid within the tank and the circulation conduit.

2. The biochemical reactor of claim 1, further comprising a ring disposed above a periphery of the second divider.

3. The biochemical reactor of claim 2, further comprising a sealant disposed between the ring and the second divider such that, responsive to a deformation of the second divider, the immobilized carriers are entrapped between the first divider and the second divider.

4. The biochemical reactor of claim 1, wherein the grating comprises fiberglass grating.

5. The biochemical reactor of claim 4, wherein the grating further comprises a resin coating.

6. The biochemical reactor of claim 4, wherein the fiberglass grating has a thickness of four inches.

7. The biochemical reactor of claim 1, wherein the grating comprises stainless steel grating.

8. The biochemical reactor of claim 7, wherein the stainless steel grating has a thickness of two inches.

9. The biochemical reactor of claim 1 wherein the support structure further comprises a hollow tube disposed between the grating and the second end, the hollow tube coupled to the grating and the second end along the central axis of the circulation conduit, the hollow tube configured to provide support for the grating.

* * * * *